United States Patent [19]

Bell

[11] Patent Number: 5,176,735
[45] Date of Patent: * Jan. 5, 1993

[54] METHOD OF DESICCATING PLANTS EMPLOYING 3-CARBONYLPHENYL URACIL DERIVATIVES

[75] Inventor: Allyn R. Bell, Cheshire, Conn.

[73] Assignee: Uniroyal Chemical Company, Inc., Middlebury, Conn.

[*] Notice: The portion of the term of this patent subsequent to Jul. 24, 2007 has been disclaimed.

[21] Appl. No.: 546,196

[22] Filed: Jun. 28, 1990

[51] Int. Cl.⁵ ............................................. A01N 43/54
[52] U.S. Cl. .................................. 504/168; 504/155; 504/241; 504/243
[58] Field of Search .................... 71/73, 74, 69, 92

[56] References Cited

U.S. PATENT DOCUMENTS

| | | | |
|---|---|---|---|
| 4,627,872 | 12/1986 | Schwamborn et al. | 71/74 |
| 4,943,309 | 7/1990 | Bell | 71/66 |

FOREIGN PATENT DOCUMENTS

| | | |
|---|---|---|
| 195346 | 3/1986 | European Pat. Off. |
| 255047 | 7/1987 | European Pat. Off. |
| 260621 | 9/1987 | European Pat. Off. |
| 9100278 | 6/1989 | PCT Int'l Appl. |

Primary Examiner—Richard L. Raymond
Assistant Examiner—B. Bembemzk
Attorney, Agent, or Firm—Raymond D. Thompson

[57] ABSTRACT

A method of desiccating plants, which method involves the application of a desiccatingly effective amount of certain 3-carbonylphenyl uracil compounds to the locus of the plants to be treated. Such application will act as a harvest aid for field crops.

3 Claims, No Drawings

METHOD OF DESICCATING PLANTS EMPLOYING 3-CARBONYLPHENYL URACIL DERIVATIVES

FIELD OF THE INVENTION

This invention is directed to a method of regulating the growth of plants, which method involves the application of a plant growth regulatory effective amount of certain 3-carbonylphenyl uracil compounds to the locus of the plants to be treated. Such application will act as a harvest aid for field crops as well as a growth retardant for aquatic species.

BACKGROUND OF THE INVENTION

One field of plant growth regulation which has become particularly economically important is the field of harvest aid compounds. The field of harvest aid utilization includes a wide variety of primary effects, including the defoliation of the corp plant; the desiccation of its leaves, stems, and other aerial organs; the control of late-season regrowth (e.g., for cotton); the promotion or inhibition of fruit or flower abscission; the concentration of crop maturity; and the enhancement of consumer-preferred quality factors.

Under normal conditions, many crop plants do not mature uniformly or in a timely fashion that would facilitate an efficient and optimum harvest, either due to equipment scheduling or weather considerations. Crops such as cotton, potato, sunflower, alfalfa and seed legumes require either desiccation or defoliation before harvest can be effectively accomplished. Thus, for example, when cotton is not defoliated the leaves can interfere with mechanized picking apparati which are frequently employed. Also, leaves can contaminate the cotton lint with trash or green stain, which reduces the quality of the fiber or reduces the efficiency of the ginning process. Likewise, potato vines need to be desiccated for efficient mechanical digging. In addition, upon desiccation of potato leaves and stems, the tuber skin matures and becomes less susceptible to damage from the digger and postharvest handling. Seed legumes and sunflowers are also mechanically harvested, and this process is facilitated if the leaves and stems are removed or desiccated. As with cotton and potato, such defoliation or desiccation also ripens the seed uniformly, accelerates the rate of seed maturation, and conditions the pod or head for easy harvest. In addition, the mechanical harvest of many fruit species, such as citrus, grape and olive, is routinely facilitated by the application of chemical abscission inducing agents.

Moreover, a major problem in many areas is the uncontrolled growth of aquatic weeds such as water hyacinth, water lettuce, duckweed and the like. Because such weeds are often located in ecologically fragile areas, it is not desirable to treat such plants with the large dosages of herbicides necessary to effectively control such plants in their aqueous environs. Rather, resort to natural control, —i.e., insects which feed off such plants—has been the desired method of treatment. Unfortunately, the growth rates of many of these species to so rapid that such natural means of control is ineffective to adequately prevent such weeds from clogging waterways. Accordingly, it would be desirable to possess a means of retarding the growth of these aquatic weeds without employing extensive amounts of chemicals such that such insects could consume said plants at rates equal to or in excess of such rate of growth, thereby effectively controlling said plants.

European Patent Application 195,346 discloses a class of 3-carbonylphenyl uracil derivatives which are described as being effective herbicides. Consequently, it is completely unexpected that such compounds, when applied appropriately, will act as harvest aids for several important crops. Moreover, it is surprising that such compounds, when applied in desirably low concentrations, will retard the growth of aquatic weeds such that said weeds may be then controlled by natural means.

Accordingly, it is an object of this invention to provide a method for regulating the growth of crops such that they may be more efficiently and economically harvested.

It is a further object of this invention to provide a method for retarding the growth of aquatic weeds such that said weeds may be effectively controlled by natural means.

DESCRIPTION OF THE INVENTION

This invention is directed to a method of desiccating plants, which method comprises applying to such plants a desiccatingly effective amount of a compound having the structural formula:

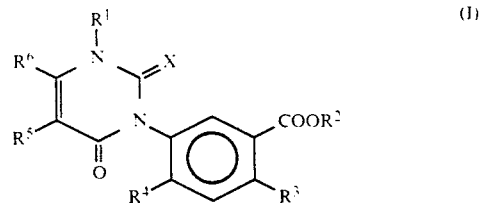

wherein:
$R^1$ is selected from the group consisting of hydrogen, $C_1$-$C_4$ alkyl, $C_2$-$C_4$ alkenyl, $C_2$-$C_4$ alkynyl, $C_2$-$C_6$ alkoxyalkyl, $C_2$-$C_6$ alkylcarbonyl, $C_2$-$C_6$ alkoxycarbonyl and formyl;
$R^2$ is selected from the group consisting of hydrogen, $C_1$-$C_6$ alkyl, $C_2$-$C_4$ alkenyl, $C_2$-$C_4$ alkynyl and $C_2$-$C_6$ alkoxyalkyl;
$R^3$ is halogen or nitro;
$R^4$ is halogen or hydrogen;
$R^5$ is selected from the group consisting of hydrogen, halogen, $C_1$-$C_4$ alkyl, monochloromethyl, monobromomethyl, $C_1$-$C_5$ alkoxymethyl, $C_1$-$C_5$ alkylthiomethyl, cyano, nitro and thiocyano;
$R^6$ is hydrogen, $C_1$-$C_4$ alkyl or $C_2$-$C_4$ fluoroalkyl; or
$R^5$ and $R^6$ together are propylidene, propylidene substituted with $C_1$-$C_3$ alkyl, butylidene, bitylidene substituted with $C_1$-$C_3$ alkyl, or form a linkage of the structure:

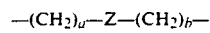
$$-(CH_2)_a-Z-(CH_2)_b-$$

wherein Z is oxygen or sulfur; and a and b are each independently 1 or 2 with the proviso that a+b is less than or equal to 3; and
X is oxygen or sulfur;
and agriculturally acceptable salts thereof.
Preferably:
$R^1$ is hydrogen, $C_1$-$C_3$ alkyl, $C_1$-$C_3$ alkenyl or $C_1$-$C_3$ alkynyl;
$R^2$ is $C_2$-$C_6$ alkyl or $C_2$-$C_6$ alkoxyalkyl;
$R^3$ is chlorine or fluorine;

$R^4$ is chlorine or fluorine;

$R^5$ is hydrogen, methyl, ethyl, monochloromethyl or monobromomethyl;

$R^6$ is hydrogen, trifluoromethyl, methyl or ethyl; and

X is oxygen.

The method of synthesis of these compounds is described in detail in European Patent Application 195,346, which disclosure is herein incorporated by reference.

In general, to synthesize compounds of the formula I in which $R^1$ denotes hydrogen and $R^2$ is $C_1$-$C_6$ alkenyl, $C_2$-$C_4$ alkynyl, or $C_2$-$C_6$ alkoxyalkyl, as well as the metallic salts of those compounds of the formula I in which $R^1$ denotes hydrogen, a compound of the general formula:

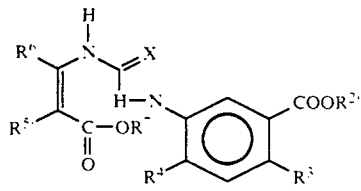

wherein $R^{2'}$ denotes $C_1$-$C_6$ alkyl, $C_2$-$C_4$ alkenyl, $C_2$-$C_4$ alkynyl or $C_2$-$C_6$ alkoxyalkyl;

$R^3$, $R^4$, $R^6$ and X have the meanings referred to above;

$R^{5'}$ denotes hydrogen, fluorine, $C_1$-$C_4$ alkyl or, together with $R^6$, an optionally modified tri- or tetramethylene as defined above in greater detail;

and $R^-$ denotes a lower alkyl, preferably $C_1$-$C_4$ alkyl, is subjected to a base catalyzed cyclization and, if desired, a possibly resulting metal salt form of the uracil derivative is converted by treatment with an acid into the corresponding acid form ($R^1$=hydrogen).

This cyclization can suitably be performed by treating the compound of the formula II in an inert, protic organic solvent, such as an alcohol, e.g. methanol, ethanol, or isopropanol; in an inert aprotic organic solvent, such as an aliphatic or cyclic ether, e.g., 1,2-dimethoxyethane, tetrahydrofuran, or dioxan, or in an aromatic compound, e.g., benzene or toluene; in an inert, aproptic polar organic solvent, e.g., dimethylformamide or dimethyl sulfoxide; with such solvents being optionally employed in a two-phase mixture with a hydrocarbon, e.g. n-hexane; or in water, with a base at temperatures between room temperature and the reflux temperature of the reaction mixture. As bases there may be considered preferably sodium alcoholates, alkali metal hydroxides, in particular sodium hydroxide and potassium hydroxide, alkali metal carbonates, in particular sodium carbonate and potassium carbonate, and sodium hydride. If an alkanol, alkenol, or alkynol is used as a solvent, then this solvent corresponds appropriately to the respective hydroxy compound $R^{2'}OH$; and thereby obviates undesired competing transesterification reactions. Upon the use of sodium hydride as base, the solvent is preferably an aliphatic or cyclic ether, dimethylformamide, or dimethyl sulfoxide.

Following completion of the cyclization, the product, upon the use of one of the above mentioned bases or the like, exists in the form of the corresponding alkali metal salt. Such product can be isolated and purified in per se known manner, or the mixture can be acidified in order to isolate the respective compound of the formula I per se. For this purpose one uses preferably an inorganic acid, such as hydrochloric acid, or a strong organic acid, such as an acetic acid or p-toluenesulfonic acid.

Other compounds employed in the practice of the method of this invention can be prepared by subjecting the appropriate intermediate (formed by the cyclization reaction described above) to the appropriate alkylation, halogenation, hydrolization, nitration or esterification reaction or treatment with the appropriate N-halosuccinimide, alcoholate, alkylmercaptan or thiocyanogen. These reactions are all well known in the art and are described in European Patent Application 195,346.

If no particular synthesis is carried out for isolating pure isomers, then the product may be obtained as a mixture of two or more isomers. The isomers can be separated according to methods known in the art. If desired, pure optically active isomers can be prepared, e.g., also by synthesis from corresponding optically active starting materials.

The synthesis of the compounds of formula II is similarly well known in the art. Thus, for example, such compounds can be produced in accordance with the following reaction scheme:

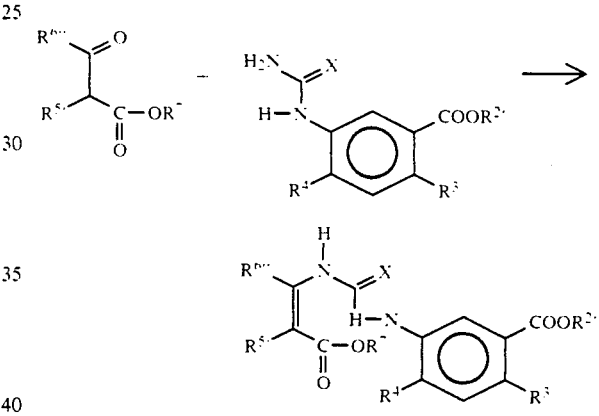

Wherein $R^{2'}$, $R^3$, $R^3$, $R^{5'}$, $R^7$ and X have the meanings referred to above; $R^6$ denotes $C_1$-$C_4$ alkyl, $C_1$-$C_4$ fluoroalkyl or, together with $R^{5'}$, possibly modified tri- or tetramethylene.

Such reaction is typically carried out by allowing the compounds to react with one another at elevated temperatures in a substantially anhydrous diluent and in the presence of an acid catalyst. As diluents there can be considered in particular organic solvents that are azeotropic with water, such as aromatic substances, e.g., benzene, toluene, and xylenes; halogenated hydrocarbons, such as methylene chloride, chloroform, carbon tetrachloride, and chlorobenzene; and aliphatic and cyclic ethers, such as 1,2-dimethoxyethane, tetrahydrofuran, and dioxan, and, as acid catalysts, in particular strong inorganic acids, such as sulfuric acid and hydrochloric acid; organic acids, such as p-toluenesulfonic acid; phosphorus-containing acids, such as orthophosphoric acid and polyphosphoric acid; and acid cation exchangers. Such reaction is typically conducted in a temperature range of from about 70° C. to 120° C., preferably at the reflux temperature of the reaction mixture. Under these reaction conditions, the desired rapid removal of the water formed in the reaction is accomplished.

The starting materials employed in the reaction scheme to make compounds of formula II are readily obtainable and/or synthesized by one of ordinary skill in the art.

The compounds employed in the method of this invention are typically utilized in the form of a composition comprised of (a) chemical (i.e., a 3-carbonylphenyl uracil derivative); and (b) a suitable carrier.

To prepare such agriculturally useful compositions, the 3-carbonylphenyl uracil compound may be mixed with an adjuvant to provide compositions in the form of finely-divided particulate solids, granules, pellets, wettable powders, flowable liquids, soluble powders, solutions, and aqueous or organic solvent dispersions or emulsions. Such formulations may be of several different physical and chemical types, any of which could be made by one familiar with the art. For instance, the agriculturally active compound may be impregnated on finely-divided or granular inorganic or organic carriers such as attapulgite clay, sand, vermiculite, corn cob, activated carbon or other granular carriers known to the art. The impregnated granules may then be spread on the soil or incorporated into the soil.

Alternatively, the chemical may be formulated as a wettable powder by grinding it into a fine powder and mixing it with an inactive powdered carrier to which a surface active dispersing agent has been added. Typical powdered solid carriers are the various mineral silicates (such as mica, talc, pyrophyllite, clays and the like) or powdered organic material (e.g., corn cob). The wettable powder may then be dispersed in water and sprayed on the soil surface, or on crop or weed plants. Alternatively, such powders could be applied directly to crop plant seeds as seed coatings.

Similarly, an emulsifiable concentrate may be prepared by dissolving the chemical in a solvent such as benzene, toluene, or other aliphatic or aromatic hydrocarbon to which a surface active dispersing agent generally has been added. The emulsifiable concentrate may then be dispersed in water and applied by spraying.

Aquatic plants, such as water hyacinth, water lettuce and the like are typically treated by spraying an an appropriate formulation onto their aerial (i.e., floating) portions.

The concentration of active chemical in the composition may vary widely typically ranging from about 0.1 to above 95% by weight. The concentration of active chemical in dispersions applied to the soil, seed or foliage is typically between about 0.002% and about 80% by weight.

Formulations containing the active ingredient(s) may be dispersed in water or an organic liquid (such as oil) and applied to target plants. Surface active agents may be added to the applied solution to increase its qualitative or quantitative range of activity. Suitable surface active agents are well known to those skilled in the art. Reference may be made to McCutcheon's Detergents and Emulsifiers (1980, Allured Publ. Co., Ridgewood, N.J.) for examples of appropriate surface active agents. Similarly, such formulations may be applied to the soil either as a liquid or a granule.

The chemical is typically applied at a rate of from about 0.01 to about 25 pounds per acre (about 0.011 to about 28 kg/ha). However, the most suitable dosage of application, and the most effective type and amount of adjuvant substance will depend on a number of factors, including the plant species; the stage of plant development; the method of application; the specific biological effect desired; the air and soil temperature and the quantity and intensity of rainfall before and after treatment; the soil type, pH, fertility and moisture and organic matter content; the physiological condition and vigor of the target plants; the relative humidity and wind velocity of the air around the crop at the time of treatment; the extent and density of the foliar canopy of the target plant; the light quality, intensity and duration each day; the type and interval of previous and subsequent crop protectant chemical applications. However, one skilled in the art can, by routine experimentation, readily determine optimum conditions for the employment of any particular substituted 3-carbonylphenyl uracil compound.

EXAMPLES

The following Examples are intended to further illustrate the invention and are not intended to limit the scope of the invention in any manner whatsoever.

EXAMPLE 1

Preparation of ethyl 2-chloro-4-fluoro-5-[3,6-dihydro-4-trifluoro methyl-2,6-dioxo-1 (2H)-pyrimidinyl] benzoate Into a 500 ml 3-necked flask equipped with a mechanical stirrer, thermometer, condenser and a nitrogen inlet tube was placed a suspension of 6.0 grams (0.15 mole) of a 60% sodium hydride dispersion in 90 ml. of dimethylformamide. The flask was chilled to $-5°$ C., and a solution of 27.5 grams (0.15 moles) of ethyl 3-amino-4,4,4-trifluorocrotonate in 55 ml. of toluene was added dropwise over a period of 30 minutes. A constant flow of nitrogen was maintained throughout the reaction. After the addition, the mixture was stirred at $0°$ C. for an additional 30 minutes before it was cooled to $-70°$ C. with a dry ice-acetone bath. Then, a solution of 36.5 grams (0.15 mole) of ethyl 5-cyanato-2-chloro-4-fluorobenzoate in 55 ml. of toluene was added dropwise at a rate while maintaining the reaction temperature at below $-60°$ C. After the addition, the thick reaction mixture was maintained at $-60°$ C. for additional 1 hour before the cooling bath was removed. The mixture was gradually warmed to room temperature and stirring was further continued for 1.5 hours. Then the mixture was poured into a solution of 15.2 ml. of concentrated hydrochloric acid in 450 ml. of water. The toluene layer was separated and the aqueous layer was further extracted twice with 200 ml. of ether. The combined organic extract was washed twice with 150 ml. of brine. Evaporation removed some of the solvent. The concentrated solution was extracted with a solution of 18 grams (0.22 mole) sodium bicarbonate in 500 ml. of water. The aqueous layer was separated. The organic later was further extracted twice with a solution of 9.0 grams (0.11 mole) of sodium bicarbonate in 80 ml. of water. The combined aqueous solution was acidified with concentrated hydrochloric acid. The white precipitate formed was extracted three times with 350 ml. of ether. Evaporation of the ether gave a viscous residue. This was further dissolved in 200 ml. of chloroform and washed three times with 30 ml. of water, then dried over anhydrous magnesium sulfate. Evaporation removed the 45.2 g (79.2%) of pale yellow viscous crude product of ethyl 2-chloro-4-fluoro-5-[3,6-dihydro-4-trifluoromethyl-2,6-dioxo-1(2H)-pyrimidinyl]benzoate.

According to NMR analysis, the product was 95%+ pure. Crystallization from $CHCl_3$/ether afforded a solid sample, m.p. 143°-4° C. 'H NMR (300 MH—, $CDCl_3$) δ

1.37 (t,3H); 4.35 (q, 2H); 6.16 (s,1H); 7.36 (d,1H); 7.86(d,1H), 10.65(s,1H).

EXAMPLE 2

Preparation of ethyl 2-chloro-4-fluoro-5-[3,6-dihydro-3-methyl-4-trifluoromethyl-2,6-dioxo-1(2H)-pyrimidinyl]benzoate (Compound 4).

Into a 100 ml. 3-necked flask equipped with a magnetic stirrer, condenser, thermometer was placed a mixture of 9.0 grams (0.024 mole) of ethyl 2-chloro-4-fluoro-5-[3,6-dihydro-4-trifluoromethyl 2,6-dioxo-1(2H)-pyrimidinyl]benzoate, 3.5 grams (0.028 mole) of dimethyl sulfate and 4.0 grams (0.048 mole) of sodium bicarbonate in 40 ml. of acetone. The mixture was heated to reflux at 60° C. for 3 hours. Evaporation removed the solvent to give a viscous residue. It was dissolved in 40 ml. of ether and washed twice with 20 ml. of water. The ether solution was dried over anhydrous magnesium sulfate. Evaporation removed the solvent to yield a viscous residue which solidified on standing. Recrystallization from 35 ml. of 20% ethylacetate in hexane afforded 8.0 grams (85%) of colorless solid, m.p. 91.5°-93.5° C., of ethyl 2-chloro-4-fluoro-5-[3,6-dihydro-3-methyl-4-trifluoromethyl-2,6-dioxo-1(2H)-pyrimidinyl]benzoate. 'H NMR (300 MHzm CDCl$_3$) δ 1.37 (t,3H); 3.55 (s,3H); 4.37 (q,2H); 6.37 (s,1H); 7.36 (d,1H); 7.88 (d,1H).

EXAMPLE 3

Preparation of 2-chloro-5-[3,6-dihydro-4-trifluoromethyl-2,6-dioxo-1(2H)pyrimidinyl]benzoic acid, Compound 19).

A mixture of 58.9 grams (0.156 mole) of isopropyl 2-chloro-5-[3,6-dihydro-4-trifluoromethyl-2,6-dioxo-1(2H) pyrimidinyl]benzoate and 11.2 grams (0.28 mole) of sodium hydroxide in 1200 ml. of 50% ethanol was heated at 65° C. for 30 minutes and stirred for 2 hours. Evaporation under a reduced pressure removed the solvent. The residue was treated with 2.3 ml. of concentrated hydrochloric acid in 130 ml. of water. Filtration collected 45 grams of crude solid. The solid product was further dissolved in a solution of 10 grams (0.25 mole) of sodium hydroxide in 600 ml. of water. The solution was cooled with an ice-water bath and then acidified to pH 2 with concentrated hydrochloric acid. The colorless precipitate was collected by filtration, rinsed with water and air-dried. The sample of 2-chloro-5-[3,6-dihydro-4-trifluoromethyl-2,6-dioxo-1 (2H) pyrimidinyl]benzoic acid weighed 40.7 grams (78%); m.p. 311°-2° C. 'H NMR (300 MHzm/DMSO-d$_6$) δ 3.36 (broad,1H); 6.37 (S,1H); 7.45 (dd, J=9.3, 2.1 Hz,1H); 7.67 (d,J=9.3 Hz,1H); 7.79 (d, J=2.1 Hz, 1H), 12.48 (broad, 1H).

EXAMPLE 4

Employing processes essentially identical to those described in Examples 1-3, several additional compounds were prepared. These compounds, along with those produced in Examples 1-3, and their melting points (for solids) or NNR characterization (for non-solids) are summarized in Table I below.

TABLE I

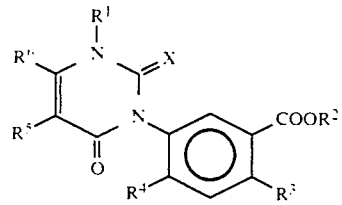

| Compound No. | X | R$^1$ | R$^2$ | R$^3$ | R$^4$ | R$^5$ | R$^6$ | Melting Point (°C.) or NMR (delta CDCl$_3$) |
|---|---|---|---|---|---|---|---|---|
| 1 | O | H | H | Cl | F | H | CF$_3$ | 270°-272° |
| 2 | O | CH$_3$ | CH$_3$ | Cl | F | H | CF$_3$ | 52°-55° |
| 3 | O | H | C$_2$H$_5$ | Cl | F | H | CF$_3$ | 143°-144° |
| 4 | O | CH$_3$ | C$_2$H$_5$ | Cl | F | H | CF$_3$ | 91.5°-93.5° |
| 5 | O | —CH$_2$CH=CH$_2$ | C$_2$H$_5$ | Cl | F | H | CF$_3$ | liquid: 1.37(t, 3H), 4.37(9.2H), 4.55(d, 2H), 5.30(m,2H), 5.88(m, 1H), 6.35(s, 1H), 7.36 (d, 1H), 7.87(d, 1H). |
| 6 | O | —CH$_2$C≡CH | C$_2$H$_5$ | Cl | F | H | CF$_3$ | liquid: 1.37(t, 3H), 2.37(s, 1H), 4.37(q, 2H), 4.70(d, 2H), 6.37(s, 1H), 7.38(d, 1H), 7.90 (d, 1H). |
| 7 | O | H | —CH(CH$_3$)$_2$ | Cl | F | H | CF$_3$ | 134°-136° |
| 8 | O | CH$_3$ | —CH(CH$_3$)$_2$ | Cl | F | H | CF$_3$ | liquid: 1.36(d, 6H), 3.57(s, 3H), 5.25(m, 1H), 6.38(s, 1H)7.37(d, 1H), 7.84(d, 1H) |

TABLE I-continued

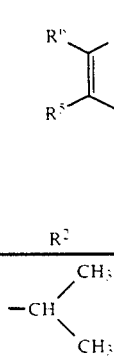

| Compound No. | X | R¹ | R² | R³ | R⁴ | R⁵ | R⁶ | Melting Point (°C.) or NMR (delta CDCl₃) |
|---|---|---|---|---|---|---|---|---|
| 9 | O | —CH₂CH=CH₂ | —CH(CH₃)₂ | Cl | F | H | CF₃ | liquid: 1.35(d, 3H), 4.55(s, 2H), 5.18(m) and 5.31(m)3H, 5.86(m, 1H), 6.36(s, 1H), 7.35 (d, 1H), 7.83(d, 1H) |
| 10 | O | H | —CH(CH₃)CH₂CH₃ | Cl | F | H | CF₃ | 150°–151° |
| 11 | O | CH₃ | —CH(CH₃)CH₂CH₃ | Cl | F | H | CF₃ | liquid: 0.96(t, 3H), 1.32(d, 3H), 1.68(m2H), 3.53(s, 3H), 5.09(hextet, 1H), 6.32(s, 1H), 7.34(d, 1H), 7.83(d, 1H) |
| 12 | O | —CH₂CH=CH₂ | —CH(CH₃)CH₂CH₃ | Cl | F | H | CF₃ | liquid: 0.95(t, 3H), 1.30(d, 3H), 1.69(m, 2H), 4.53(broad s, 1H), 5.08–5.28(m, 3H), 5.86(m, 1H), 6.35(s, 1H), 7.33(d, 1H), 7.83(d, 1H) |
| 13 | O | H | —CH(CH₂CH₃)CH₂CH₃ | Cl | F | H | CF₃ | 150°–152° |
| 14 | O | CH₃ | —CH(CH₂CH₃)CH₂CH₃ | Cl | F | H | CF₃ | liquid: 0.95(t, 6H), 1.68(m, 4H), 3.55(s, 3H), 5.02(pentet, 1H), 6.36(s, 1H), 7.37(d, 1H), 7.85(d, 1H) |
| 15 | O | CH₃ | —CH₂CH(CH₃)₂ | Cl | F | H | CF₃ | 85°–87° |
| 16 | O | CH₃ | —CH₂CH(CH₃)₂ | Cl | F | H | CF₃ | liquid: 0.99(d, 6H), 2.03(m, 1H), 3.52(s, 3H), 4.11(d, 2H), 6.37(s, 1H) |
| 17 | O | H | —CH₂CH₂OCH₃ | Cl | F | H | CF₃ | liquid: 3.36(s, 3H) |
| 18 | O | CH₃ | —CH₂CH₂OCH₃ | Cl | F | H | CF₃ | liquid: 3.36(s, 3H) |
| 19 | O | H | H | Cl | H | H | CF₃ | 311°–312° |
| 20 | O | H | —CH(CH₃)₂ | Cl | H | H | CF₃ | 184°–187° |
| 21 | O | CH₃ | —CH(CH₃)₂ | Cl | H | H | CF₃ | 111°–112° |
| 22 | O | —CH₂CH=CH₂ | —CH(CH₃)₂ | Cl | H | H | CF₃ | liquid: 1.36(d, 6H), 4.55(d, 2H), 5.28(m, 3H), 5.86(m, 1H), 6.37(s, 1H), 7.25(d, 1H), 7.55 (d, 1H), 7.69(d, 1H) |
| 23 | O | —C₂C≡CH | —CH(CH₃)₂ | Cl | H | H | CF₃ | 46°–48° |
| 24 | O | H | —CH(CH₃)CH₂CH₃ | Cl | H | H | CF₃ | 171.5°–172.5° |
| 25 | O | CH₃ | —CH(CH₃)CH₂CH₃ | Cl | H | H | CF₃ | liquid: 0.96(t, 3H), 1.35(d, 3H), 1.70(m, 2H), 3.51(s, 3H), 5.09(m, 1H), 6.34(s, 1H), 7.26 (d, 1H), 7.55(d, 1H), 7.74(d, 1H) |

TABLE I-continued

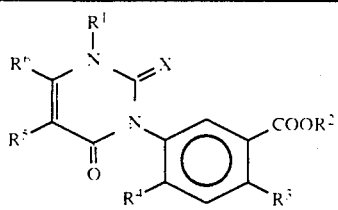

| Compound No. | X | R¹ | R² | R³ | R⁴ | R⁵ | R⁶ | Melting Point (°C.) or NMR (delta CDCl₃) |
|---|---|---|---|---|---|---|---|---|
| 26 | O | H | —CH₂CHCH₃ with CH₃ branch | Cl | H | H | CF₃ | 143°–145° |
| 27 | O | H | —CH₂CH₂OCH₃ | Cl | H | H | CF₃ | 130°–132° |
| 28 | O | CH₃ | —CH₂CH₂OCH₃ | Cl | H | H | CF₃ | liquid: 3.38(s, 3H), 3.52(s, 3H), 3.70(t, 2H), 4.46(t, 2H), 6.34(s, 1H), 7.35(d, 1H), 7.56 (d, 1H), 7.79(d, 1H) |
| 29 | O | H | —CH(CH₃)₂ | H | F | H | CF₃ | 168°–170° |
| 30 | O | CH₃ | —CH(CH₃)₂ | CH₃ | F | H | CF₃ | liquid |
| 31 | O | CH₃ | —CH(CH₃)₂ | Cl | F | F | CF₃ | wax: 1.39, (d, 6H), 3.55(s,3H), 5.25(quintet, 1H), 7.39(d, 1H), 7.85(d, 1H) |
| 32 | O | CH₃ | —CH(CH₃)₂ | Cl | F | —CH₂CH₂CH₂— | | 111°–113° |

*In the Table above:
s — singlet
d — duplet
t — triplet
q — quartet
m — multiplet

EXAMPLE 5

To illustrate the effectiveness of the described 3-carbonyl-phenyl-uracil derivatives as crop plant desiccants, 3000 ppm (mg/l) solution/suspension of active ingredient was prepared by dissolving 450 mg of each compound in 10 ml of organic solvent (usually acetone) plus 0.15 g surface active agent (Tween 20 (trademark), ethoxylated sorbitan monolaurate). This solution was then diluted to 150 ml with distilled water, giving the 3000 ppm preparation. A 1000 ppm solution/suspension was produced by further dilution with distilled water. These solution/suspension were applied to soybean *Glycine max* (L.) Merr. cv. Williams (3000 ppm) and dry bean *Phaseolus vulgaris* L. cv. Pinto III (1000 ppm) plants atomization with a DeVilbiss (trademark) Model 152 sprayer, wetting the foliage to the drip point. After 3 weeks in the greenhouse, the plants were scored for leaf desiccation on a 0 to 100 scale, 0 being no damage and 100 being complete kill. A rating system suggested by Frans and Talbert (1977. Research Methods in Weed Science, 2nd edition, Southern Weed Science Society) was used as a guide. The data obtained appear in Table II.

TABLE II

| COMPOUND NUMBER | PERCENT DESICCATION | |
|---|---|---|
| | SOYBEANS (3000 ppm) | BEANS (1000 ppm) |
| 1 | 20 | 0 |
| 2 | 100 | * |
| 3 | 10 | 10 |
| 4 | 100 | 100 |
| 5 | 100 | 100 |
| 6 | 100 | 100 |
| 7 | 60 | 45 |
| 8 | 100 | 100 |
| 9 | 100 | 100 |
| 10 | 100 | 95 |
| 11 | 100 | 100 |
| 12 | 90 | 100 |
| 13 | 45 | 20 |
| 14 | 100 | 100 |
| 15 | 95 | 100 |
| 16 | 100 | 100 |
| 17 | 85 | 5 |
| 18 | 100 | 100 |
| 19 | 30 | 100 |
| 20 | 10 | 5 |
| 21 | 100 | 100 |
| 22 | 95 | 100 |
| 23 | 95 | 100 |
| 24 | 100 | 20 |
| 25 | 100 | 100 |
| 26 | 100 | 100 |

TABLE II-continued

| COMPOUND NUMBER | PERCENT DESICCATION SOYBEANS (3000 ppm) | BEANS (1000 ppm) |
|---|---|---|
| 27 | 25 | 0 |
| 28 | 100 | 100 |
| 29 | 10 | 0 |
| 30 | 100 | 100 |
| 31 | 100 | 100 |
| 32 | 100 | 100 |

* not tested

EXAMPLE 6

To illustrate the effectiveness of the above-mentioned compounds as crop harvest aids, potato plants (Solanum tuberosum L. cv. Pontiac) were sown approximately 0.3 meter apart in rows 1.5 meters on wide and 4.6 meters long. Approximately 3 months after planting, the aerial portions of the plants were treated with aqueous solutions of an emulsifiable concentrate formulation of compound 8 at rates given in Table III. The spray solutions were applied at 360 liters/hectare and contained 0.04% by volume of spreader (X-77 (trademark), Chevron Chem. Co.; a mixture of alkyaryl polyoxethylene glycols, free fatty acids and isopropanol). In this test, the treatments were replicated five times. Eleven days after treatment (DAT), the plots were evaluated for percentage vine kill and averaged. The results are summarized in Table III.

TABLE III

| Field Test to Evaluate Potato Vine Kill | | | |
|---|---|---|---|
| Compound | Rate (a.i.) lb/A | kg/ha | % Vine Kill (11 DAT) |
| 8 | 0.063 | 0.07 | 92 |
|  | 0.125 | 0.14 | 98 |
|  | 0.25 | 0.28 | 97 |
| paraquat | 0.5 | 0.56 | 83 |
| untreated | — | — | 0 |

EXAMPLE 7

Field Trial to Evaluate Potato Vine Desiccation

To further illustrate the effectiveness of the above-mentioned compounds as crop harvest aids, potato plants (cv. Russet Burbank) were field grown in a fashion similar to that described in Example 6. Compounds 8 and 21 were applied to the aerial portions of the plants in late season in a spray volume of 375 L/ha, without surface active agent. The plots were evaluated 10 days after treatment, and the results are summarized in Table IV.

TABLE IV

| Field Trial to Evaluate Potato Vine Desiccation | | | | |
|---|---|---|---|---|
| Compound | Rate a.i. lb/A | kg/ha | % Desiccation (10 DAT) leaf | stem |
| 8 | 0.032 | 0.035 | 85 | 80 |
|  | 0.063 | 0.07 | 98 | 90 |
|  | 0.125 | 0.14 | 100 | 95 |
| 21 | 0.063 | 0.07 | 80 | 50 |
|  | 0.125 | 0.14 | 90 | 85 |
|  | 0.25 | 0.28 | 100 | 95 |
| diquat | 0.5 | 0.56 | 100 | 95 |
| untreated | — | — | 7 | 5 |

EXAMPLE 8

To further illustrate the effectiveness of the above-mentioned compounds as harvest aids, Texas' high plains "stripper" cotton (Gossypium hirsutum L.) was field grown in 1 meter wide rows 9.1 meter long until the bolls were 30 to 40% open. Aqueous spray solutions of the compounds tested were applied to the aerial portions of the plant in a volume of 140 L/ha. Spreader/sticker (X-77 (trademark), Chevron Chem. Co.) was used at a 0.25% by volume rate. In this test, the treatments were replicated three times. The plots were evaluated 18 days after treatment, and the results were summarized in Table V.

TABLE V

| Compound | Rate (a.i.) lb/A | kg/ha | % Defoliation (18 DAT) |
|---|---|---|---|
| 8 | 0.03 | 0.03 | 53 |
|  | 0.06 | 0.07 | 62 |
|  | 0.12 | 0.13 | 67 |
| 21 | 0.06 | 0.07 | 48 |
|  | 0.12 | 0.13 | 50 |
|  | 0.24 | 0.27 | 57 |
| paraquat | 0.25 | 0.28 | 53 |
| arsenic acid | (1 quart) | (2.3 L/ha) | 47 |
| untreated | — | — | 25 |

EXAMPLE 9

In order to test the effectiveness of the present claimed process on aquatic weeds, a formulation of Compound 8 in toluene and Sponto ™ N-500B (believed to be a blend of oil-soluble sulfonates with polyoxyethylene ethers; available from Witco Chemical Corp.) was sprayed (at the concentrations listed in Table VI below) on the aerial portions of water hyacinth. The root lengths of the treated samples were compared with that of untreated samples. The results of such comparison (i.e., the average of 5 replications) are presented in Table VI.

TABLE VI

| Concentration (ounces of active ingredient/ 100 gallons/acre) | Root Length (mm) |
|---|---|
| 0 | 13.2 |
| 0.5 | 4.6 |
| 0.25 | 3.1 |
| 0.125 | 3.4 |

The above results are significant in that they will enable predators of water hyacinth, such as the water hyacinth weevil (Neochetina eichorniae or Nenochetina bruchi), to consume such weeds at rates in excess of their growth. This method of control is far superior to herbicidal means as the use of herbicides will result in dead plants clogging waterways whereas such a plant growth regulant/predator combination will result in the natural removal of water weeds from waterways.

EXAMPLE 10

To further illustrates the effectiveness of the compounds of this invention as crop harvest aids, rapeseeds were grown to the pre-harvest stage and Compound 21 was applied to aerial portions of the plants together with a crop oil concentrate (COC) at the rates (pounds per acre (lb.A) and quarts per acre (qt./A)) indicated in the following Table VII which also contains the results realized fourteen days after treatment (DAT)).

TABLE VII

| Rate | % Desiccation (Leaf) | % Desiccation (Pod) | % Defoliation (Leaf) |
|---|---|---|---|
| 0.03 lb/A 1.00 qt/A | 55.0 | 83.3 | 80.0 |
| 0.06 lb/A 1.00 qt/A | 60.0 | 90.0 | 85.0 |
| 0.125 lb/A 1.00 qt/A | 85.0 | 96.7 | 83.3 |

EXAMPLE 11

Navy Beans were grown to the early pod yellow stage and Compound 21 was applied to aerial portions of the plants together with a crop oil concentrate (COC) at the rates (pounds per arce (lb/A) and quarts per acre (qt/A)) indicated in the following Table VIII which also contains the results realized seven days after treatment (DAT).

TABLE VIII

| Rate | % Desiccation (Leaf) |
|---|---|
| 0.0312 lb/A 1.000 qt/A | 88.8 |
| 0.625 lb/A 1.000 qt/A | 90.0 |
| 0.125 lb/A 1.000 qt/A | 97.3 |

What is claimed is:

1. A method of desiccating field crop plants, which method comprises applying to such plants a desiccatingly effective amount of a compound having the structural formula:

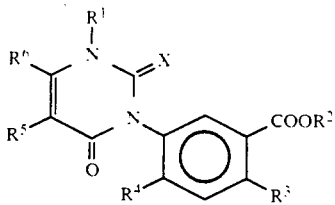

wherein:
$R^1$ is hydrogen, $C_1$-$C_3$ alkyl, $C_1$-$C_3$ alkenyl or $C_1$-$C_3$ alkynyl;
$R^2$ is $C_2$-$C_6$-alkyl or $C_2$-$C_6$ alkoxyalkyl;
$R^3$ is chlorine or fluorine;
$R^4$ is chlorine, hydrogen or fluorine;
$R^5$ is hydrogen, methyl, ethyl, monochloromethyl or monobromomethyl;
$R^6$ is hydrogen, trifluoromethyl, methyl or ethyl; and
X is oxygen.

2. A method in accordance with claim 1 wherein X is oxygen; $R^1$ is methyl; $R^2$ is isopropyl $R^3$ is chloro; $R^4$ is fluoro; $R^5$ is hydrogen; and $R^6$ is trifluoromethyl.

3. A method in accordance with claim 1 wherein said crops are selected from the group consisting of potatoes, soybeans, beans, alfalfa and rapeseed.

* * * * *